US00PP25124P2

(12) United States Plant Patent
van der Knaap

(10) Patent No.: US PP25,124 P2
(45) Date of Patent: Nov. 25, 2014

(54) ***CURCUMA* PLANT NAMED 'CURALIMEI'**

(50) Latin Name: *Curcuma alismatifolia*
Varietal Denomination: Curalimei

(71) Applicant: Leonardus Johannes Maria van der Knaap, Naaldwijk (NL)

(72) Inventor: Leonardus Johannes Maria van der Knaap, Naaldwijk (NL)

(73) Assignee: Nubilus B.V., Naaldwijk (NL)

( * ) Notice: Subject to any disclaimer, the term of this patent is extended or adjusted under 35 U.S.C. 154(b) by 0 days.

(21) Appl. No.: 13/987,345

(22) Filed: Jul. 15, 2013

(51) Int. Cl.
*A01H 5/00* (2006.01)

(52) U.S. Cl.
USPC ..... Plt./421

(58) Field of Classification Search
CPC ..... A01H 5/00
USPC ..... Plt./421
See application file for complete search history.

*Primary Examiner* — Anne Grunberg
(74) *Attorney, Agent, or Firm* — C. A. Whealy

(57) ABSTRACT

A new and distinct cultivar of *Curcuma* plant named 'Curalimei', characterized by its upright and columnar plant habit with outwardly arching leaves; freely clumping growth habit; leaves with dark purple-colored midveins; freely flowering habit; flowers with dark pink-colored flower bracts and dark red purple-colored apices that are positioned just above the foliar plane on strong and erect peduncles.

2 Drawing Sheets

Botanical designation: *Curcuma alismatifolia.*
Cultivar denomination: 'CURALIMEI'.

BACKGROUND OF THE INVENTION

The present invention relates to a new and distinct cultivar of *Curcuma* plant, botanically known as *Curcuma alismatifolia* and hereinafter referred to by the name 'Curalimei'.

The new *Curcuma* plant is a product of a controlled breeding program conducted by the Inventor in Naaldwijk, The Netherlands. The objective of the breeding program is to create new *Curcumas* that have uniform plant habit, good container performance and attractive inflorescence coloration.

The new *Curcuma* plant originated from a cross-pollination made by the Inventor in June, 2009 in Naaldwijk, The Netherlands of a proprietary selection of *Curcuma alismatifolia* identified as code number 20061748-026, not patented, as the female, or seed, parent with a proprietary selection of *Curcuma alismatifolia* identified as code number 20041713-001, not patented, as the male, or pollen, parent. The new *Curcuma* plant was discovered and selected by the Inventor as a single flowering plant within the progeny of the stated cross-pollination in a controlled greenhouse environment in Naaldwijk, The Netherlands in August, 2010.

Asexual reproduction of the new *Curcuma* plant by tissue culture in a controlled environment in Maasdijk, The Netherlands since September, 2010 has shown that the unique features of this new *Curcuma* plant are stable and reproduced true to type in successive generations of asexual reproduction.

SUMMARY OF THE INVENTION

Plants of the new *Curcuma* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Curalimei'. These characteristics in combination distinguish 'Curalimei' as a new and distinct *Curcuma* plant:

1. Upright and columnar plant habit with outwardly arching leaves.
2. Freely clumping growth habit.
3. Leaves with dark purple-colored midveins.
4. Freely flowering habit.
5. Flowers with dark pink-colored flower bracts and dark red purple-colored apices that are positioned just above the foliar plane on strong and erect peduncles.

Plants of the new *Curcuma* differ from plants of the female parent selection in the following characteristics:

1. Plants of the new *Curcuma* are taller than plants of the female parent selection.
2. Plants of the new *Curcuma* and the female parent selection differ in leaf color as plants of the female parent selection have leaves with green-colored midveins.

Plants of the new *Curcuma* differ from plants of the male parent selection in the following characteristics:

1. Plants of the new *Curcuma* have larger flowers than plants of the male parent selection.
2. Plants of the new *Curcuma* and the male parent selection differ in flower bract color as plants of the male parent selection have lighter pink-colored flower bracts.

Plants of the new *Curcuma* can also be compared to plants of *Curcuma alismatifolia* 'Curzena', disclosed in U.S. Plant Pat. No. 19,956. In side-by-side comparisons conducted in Naaldwijk, The Netherlands, plants of the new *Curcuma* differed from plants of 'Curzena' in the following characteristics:

1. Plants of the new *Curcuma* were more freely clumping than plants of 'Curzena'.
2. Plants of the new *Curcuma* were more freely flowering than plants of 'Curzena'.

3. Plants of the new *Curcuma* and 'Curzena' differed in flower bract color as plants of 'Curzena' had lighter pink-colored flower bracts.

BRIEF DESCRIPTION OF THE PHOTOGRAPHS

The accompanying photographs illustrate the overall appearance of the new *Curcuma* showing the colors as true as it is reasonably possible to obtain in colored reproductions of this type. Colors in the photographs may differ slightly from the color values cited in the detailed botanical description which accurately describe the colors of the new *Curcuma* plant.

The photograph on the first sheet is a side perspective view of a typical plant of 'Curalimei' grown in a container.

The photograph on the second sheet is a close-up view of a typical flower plant of 'Curalimei'.

DETAILED BOTANICAL DESCRIPTION

The aforementioned photographs and following observations and measurements describe plants grown during the spring in 14-cm containers in a glass-covered greenhouse in Naaldwijk, The Netherlands and under cultural practices typical of commercial *Curcuma* production. During the production of the plants, day temperatures ranged from 22° C. to 28° C., night temperatures ranged from 20° C. to 22° C. and light levels averaged 55 kilolux. Plants were 19 weeks old when the photographs and the detailed description were taken. In the following description, color references are made to The Royal Horticultural Society Colour Chart, 2007 Edition, except where general terms of ordinary dictionary significance are used.

Botanical classification: *Curcuma alismatifolia* 'Curalimei'.

Parentage:

*Female, or seed, parent*.—Proprietary selection of *Curcuma alismatifolia* identified as code number 20061748-026, not patented.

*Male, or pollen, parent*.—Proprietary selection of *Curcuma alismatifolia* identified as code number 20041713-001, not patented.

Propagation:

*Type*.—By tissue culture.

*Time to initiate roots*.—About ten days at temperatures about 23° C.

*Time to produce a rooted young plant*.—About 28 to 30 days at temperatures about 21° C.

*Root description*.—Medium in thickness, fibrous; close to 155A in color.

*Rooting habit*.—Moderately branching, medium density.

*Number of rhizomes produced per plant*.—About nine.

*Rhizome diameter*.—About 6 mm.

Plant description:

*Growth habit*.—Upright and columnar with outwardly arching leaves; freely clumping habit.

*Plant height (soil level to top of inflorescences)*.—About 46.3 cm.

*Plant diameter*.—About 37.9 cm.

Leaf description:

*Leaf arrangement*.—Alternate; simple.

*Length, fully expanded*.—About 40.1 cm.

*Width, fully expanded*.—About 4.3 cm.

*Shape*.—Lanceolate to narrowly elliptic.

*Apex*.—Acuminate.

*Base*.—Sheathing; wings, about 11 cm in length and about 1 cm in width.

*Margin*.—Entire; slightly undulate.

*Venation*.—Pinnate.

*Aspect*.—Initially upright, then about 45° from vertical.

*Texture*.—Smooth, glabrous.

*Color*.—Developing and fully expanded leaves, upper surface: Close to 137B; midvein, close to N186C; secondary venation, close to 137B. Developing and fully expanded leaves, lower surface: Between 137B and N138B; midvein, close to N138C; secondary venation, close to between 137B and N138B.

Inflorescence description:

*Arrangement*.—Dense terminal spike inflorescences develop directly from the rhizome with numerous bracts and bracteole flowers in bract axils.

*Time to flower*.—In The Netherlands, plants flower from spring into autumn; flowering continuous during this period.

*Flower longevity*.—Flowers last about three days on the plant; flowers not persistent.

*Fragrance*.—None detected.

*Inflorescence length*.—About 13.6 cm.

*Inflorescence diameter*.—About 8 cm.

*Flowers*.—Length: About 3.9 cm. Diameter: About 1.2 cm. Shape: Zygomorphic with three petals; lower petal (labellum) is conspicuous; calyx with three sepals. Color: Upper petal, upper surface: Close to 83A to 83C; markings towards the base, close to 17A to 17B. Upper petal, lower surface: Close to 79B to 79C. Lower petals (labellum), upper and lower surfaces: Close to NN155B; towards the apex, flushed with close to 84D.

*Flower bracts*.—Quantity: About 14 per inflorescence. Length, upper bracts: About 6.8 cm. Width, upper bracts: About 5 cm. Length, lower bracts: About 3.3 cm. Width, upper bracts: About 5 cm. Shape, upper bracts: Ovate. Shape, lower bracts: Orbicular. Apex, all bracts: Obtuse. Base, all bracts: Fused. Margin, all bracts: Entire. Texture, all bracts, upper and lower surfaces: Smooth, glabrous. Color: Upper bracts, upper surface: Close to 72C and N74C; towards the apex, close to 59A to 59B. Upper bracts, lower surface: Between 72C and 74D; towards the apex, close to 187A. Lower bracts, upper surface: Close to 144C and 145A; irregular markings, close to 59A. Upper bracts, lower surface: Close to 144B to 144C; irregularly markings, close to 59A.

*Peduncles*.—Length: About 31.2 cm. Diameter: About 6 mm. Texture: Smooth, glabrous. Angle: Upright, erect. Color: Between 138A and 143A.

*Stamens*.—Quantity: Two per flower. Filament: Length: About 9 mm. Diameter: About 2.5 mm. Color: Close to NN155B; towards the apex, close to N82B to N82C. Anther color: Close to 155B. Pollen amount: Moderate. Pollen color: Close to NN155A to NN155B.

*Pistils*.—Quantity per flower: One. Pistil length: About 1.9 cm. Stigma: Length: About 2 mm. Diameter: About 2 mm. Color: Close to 155A. Style: Length: About 1.7 cm. Diameter: About 0.5 mm. Color: Close to NN155B.

*Seeds and fruits*.—Seed and fruit development have not been observed on plants of the new *Curcuma*.

Disease & pest resistance: Plants of the new *Curcuma* have not been observed to be resistant to pathogens or pests common to *Curcuma*.

Temperature tolerance: Plants of the new *Curcuma* have been observed to be tolerant to temperatures ranging from about 15° C. to about 30° C.

It is claimed:

1. A new and distinct *Curcuma* plant named 'Curalimei' as illustrated and described.

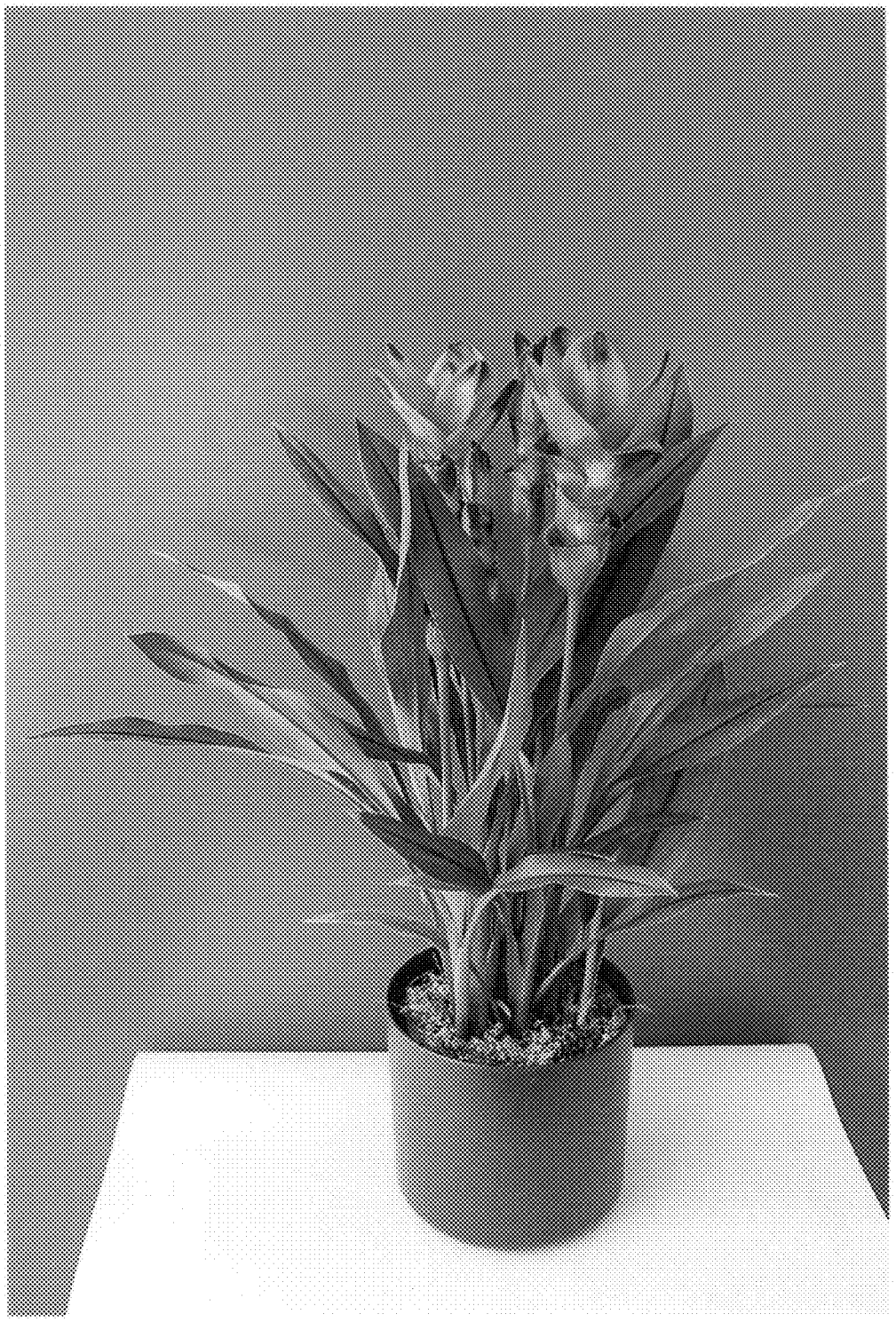

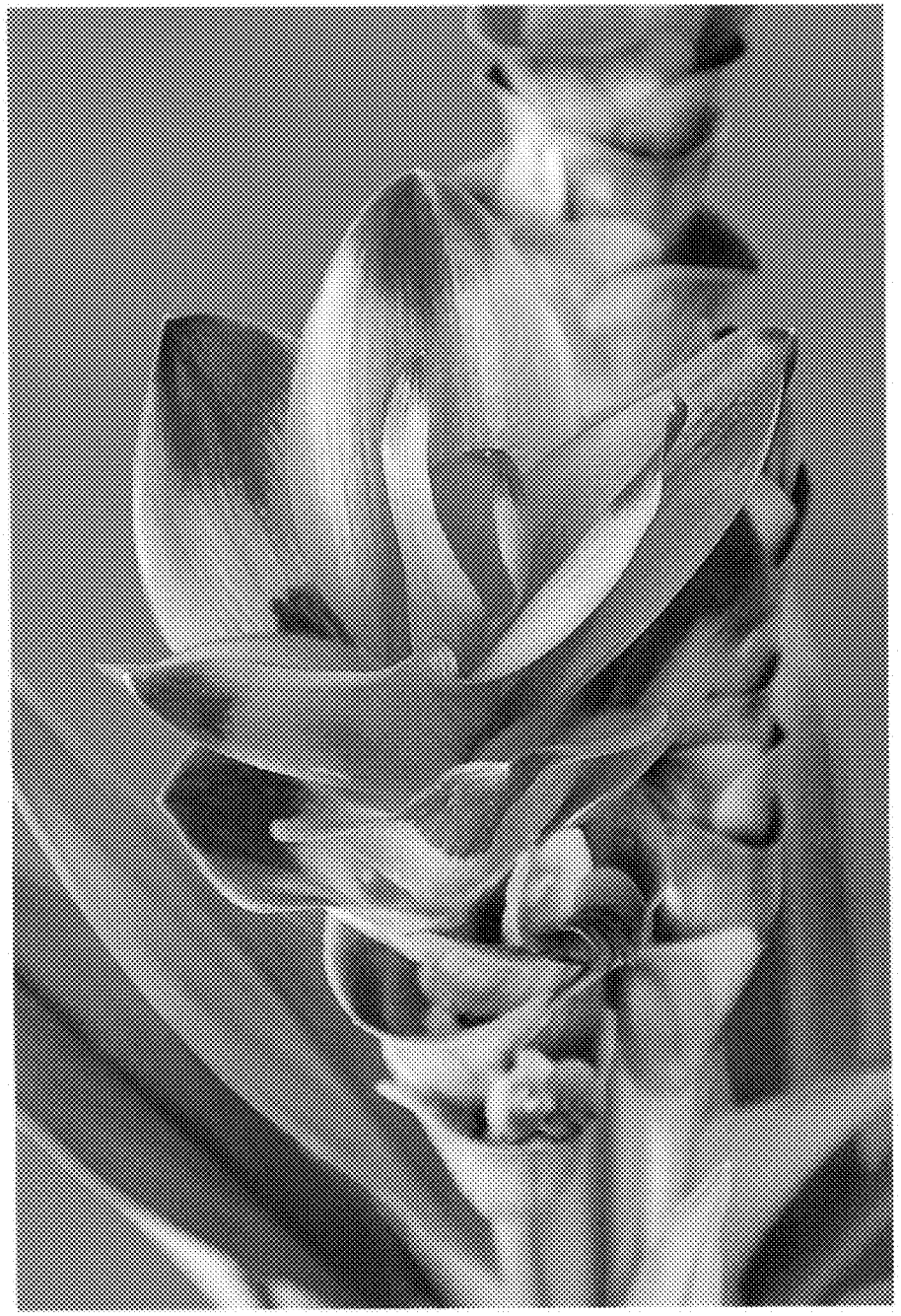

* * * * *